(12) United States Patent
Dascola et al.

(10) Patent No.: US 11,798,277 B2
(45) Date of Patent: *Oct. 24, 2023

(54) USER SCANNING AND ONE-WAY AUGMENTED REALITY VIEWING SYSTEM

(71) Applicant: TRUIST BANK, Charlotte, NC (US)

(72) Inventors: Michael Anthony Dascola, Clayton, NC (US); Jacob Atticus Grady, Raleigh, NC (US); Kaitlyn Stahl, Raleigh, NC (US)

(73) Assignee: Truist Bank, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/580,871

(22) Filed: Jan. 21, 2022

(65) Prior Publication Data

US 2022/0148306 A1 May 12, 2022

Related U.S. Application Data

(62) Division of application No. 16/915,009, filed on Jun. 29, 2020, now Pat. No. 11,295,134.

(Continued)

(51) Int. Cl.
*G06V 20/20* (2022.01)
*G06F 3/01* (2006.01)
(Continued)

(52) U.S. Cl.
CPC .............. *G06V 20/20* (2022.01); *A61B 5/112* (2013.01); *G06F 3/013* (2013.01); *G06F 21/32* (2013.01);
(Continued)

(58) Field of Classification Search
CPC ...... G06V 20/20; G06V 40/171; G06T 7/207; G06T 7/74; A61B 5/112; G06F 3/013;
(Continued)

(56) References Cited

U.S. PATENT DOCUMENTS

2014/0232750 A1 8/2014 Price
2015/0032556 A1 1/2015 Evans et al.
(Continued)

OTHER PUBLICATIONS

Non-Final Office Action, U.S. Appl. No. 17/671,699, filed Nov. 14, 2022, 22 pages.
(Continued)

*Primary Examiner* — Jin Ge
(74) *Attorney, Agent, or Firm* — Kilpatrick Townsend & Stockton LLP; Michael A. Springs, Esq.

(57) ABSTRACT

An augmented reality customer interaction system includes a transparent panel having a first side and a second side that is opposite to the first side, and a camera device configured to capture visual data from an area adjacent to the second side of the transparent panel. The visual data includes identifying features of a customer located in the area with respect to the second side of the transparent panel. The system further includes a projection system configured to project information on the first side of the transparent panel. The information projected on the first side of the transparent panel may include customer interaction data retrieved from a data store based on the identifying features of the customer.

13 Claims, 9 Drawing Sheets

Related U.S. Application Data

(60) Provisional application No. 62/869,715, filed on Jul. 2, 2019.

(51) Int. Cl.
| | | |
|---|---|---|
| *G06F 21/32* | (2013.01) | |
| *G06T 7/207* | (2017.01) | |
| *G06T 7/73* | (2017.01) | |
| *A61B 5/11* | (2006.01) | |
| *H04L 9/40* | (2022.01) | |
| *G06Q 30/0251* | (2023.01) | |
| *G06V 40/16* | (2022.01) | |

(52) U.S. Cl.
CPC ......... *G06Q 30/0269* (2013.01); *G06T 7/207* (2017.01); *G06T 7/74* (2017.01); *G06V 40/171* (2022.01); *H04L 63/105* (2013.01); *H04L 2463/082* (2013.01)

(58) Field of Classification Search
CPC ... G06F 21/32; G06Q 30/0269; H04L 63/105; H04L 2463/082
USPC .......................................................... 345/633
See application file for complete search history.

(56) References Cited

U.S. PATENT DOCUMENTS

| | | | |
|---|---|---|---|
| 2016/0378861 A1 | 12/2016 | Eledath et al. | |
| 2017/0031575 A1 | 2/2017 | Dotan-Cohen et al. | |
| 2017/0060512 A1* | 3/2017 | Rakshit | G06F 3/041 |
| 2017/0351909 A1* | 12/2017 | Kaehler | G06K 9/6215 |
| 2018/0033171 A1* | 2/2018 | Rakshit | G06T 11/60 |
| 2018/0115696 A1* | 4/2018 | Wexler | G06Q 50/01 |
| 2018/0275504 A1* | 9/2018 | Ono | G03B 21/10 |
| 2018/0284453 A1 | 10/2018 | Irvin et al. | |
| 2019/0094981 A1* | 3/2019 | Bradski | G06F 3/017 |
| 2019/0095925 A1 | 3/2019 | Gabriele et al. | |
| 2019/0385214 A1 | 12/2019 | Melcher et al. | |
| 2020/0125322 A1* | 4/2020 | Wilde | G06F 1/163 |
| 2020/0250766 A1 | 8/2020 | Sancheti et al. | |

OTHER PUBLICATIONS

Non-Final Office Action, U.S. Appl. No. 17/671,699, filed Jun. 27, 2023 27 pages.

* cited by examiner

USER SCANNING AND ONE-WAY AUGMENTED REALITY VIEWING SYSTEM

CROSS-REFERENCE TO RELATED APPLICATIONS

This application is a divisional of U.S. patent application Ser. No. 16/915,009, filed on Jun. 29, 2020, and titled "User Scanning and One-Way Augmented Reality Viewing System," which claims priority to U.S. Provisional Patent Application No. 62/869,715, filed on Jul. 2, 2019, and titled "User Scanning and One-Way Augmented Reality Viewing System," the disclosure of which is hereby incorporated by reference in its entirety.

TECHNICAL FIELD

The present disclosure relates generally to user detection and authentication systems, including sensor systems to detect and identify users. The present disclosure also relates to one-way augmented reality systems to provide information for interacting with users.

BACKGROUND

Customer service representatives at locations such as banks or other financial institutions, as well as other retail locations (e.g., stores, restaurants, etc.), interact with many customers on a daily basis. In some cases, the interactions may be live, where the customers and the customer service representatives are at the same location. In other cases, the customer service representatives may be at a location remote from the customer location. In either case, a customer service representative may have no knowledge regarding the identity or motives of a person entering the location. For example, a customer may be a client, e.g., a person that frequently visit a particular location, such as a bank. Alternatively, a customer may be a prospective client seeking the services provided at the location. In other cases, the customer may be a fraudster attempting to defraud a business, for example, by passing a bad check mitigate risk of fraud, money laundering and other forms of theft. In any of these scenarios, information regarding the person entering the location as well as the person's motives may not be available to the customer service representatives to enable them to take appropriate action with regard to a particular customer.

SUMMARY

In one example, an augmented reality user interaction system may include a processing unit including a processor, a camera device configured to capture sensor data about a location, and to capture visual data about an object in the location, a computer-readable memory having stored thereon instructions that are executable by the processor. The instructions may cause the system to receive the sensor data corresponding to the location from the camera device, the sensor data including the visual data, analyze the sensor data to detect a user within a proximity of the location, detect, based on analyzing the sensor data, a characteristic of the user, compare the characteristic of the user to a data store having a plurality of user profiles with user characteristics stored therein for a plurality of users, identify a user profile among the plurality of user profiles by matching the characteristic to a user characteristic associated with the user profile, and generate and output user interaction data associated with the user profile via an augmented reality system.

In another example, an augmented reality customer interaction system may include a transparent panel having a first side and a second side that is opposite to the first side, and a camera device configured to capture visual data from an area adjacent to the second side of the transparent panel. The visual data may include identifying features of a customer located in the area with respect to the second side of the transparent panel. The system may further include a projection system configured to project information on the first side of the transparent panel. The information projected on the first side of the transparent panel may include customer interaction data retrieved from a data store based on the identifying features of the customer.

In a further example, a method for providing augmented reality content may include identifying a customer at a customer interaction location, retrieving customer-specific interaction data, determining locations of a customer service representative in an area adjacent to a first side of a transparent panel and the customer in an area adjacent to a second side of the transparent panel, and projecting an augmented reality element to the first side of a transparent panel, the augmented reality element displaying the customer-specific interaction data on the first side of the transparent panel.

DETAILED DESCRIPTION

Figure 1:
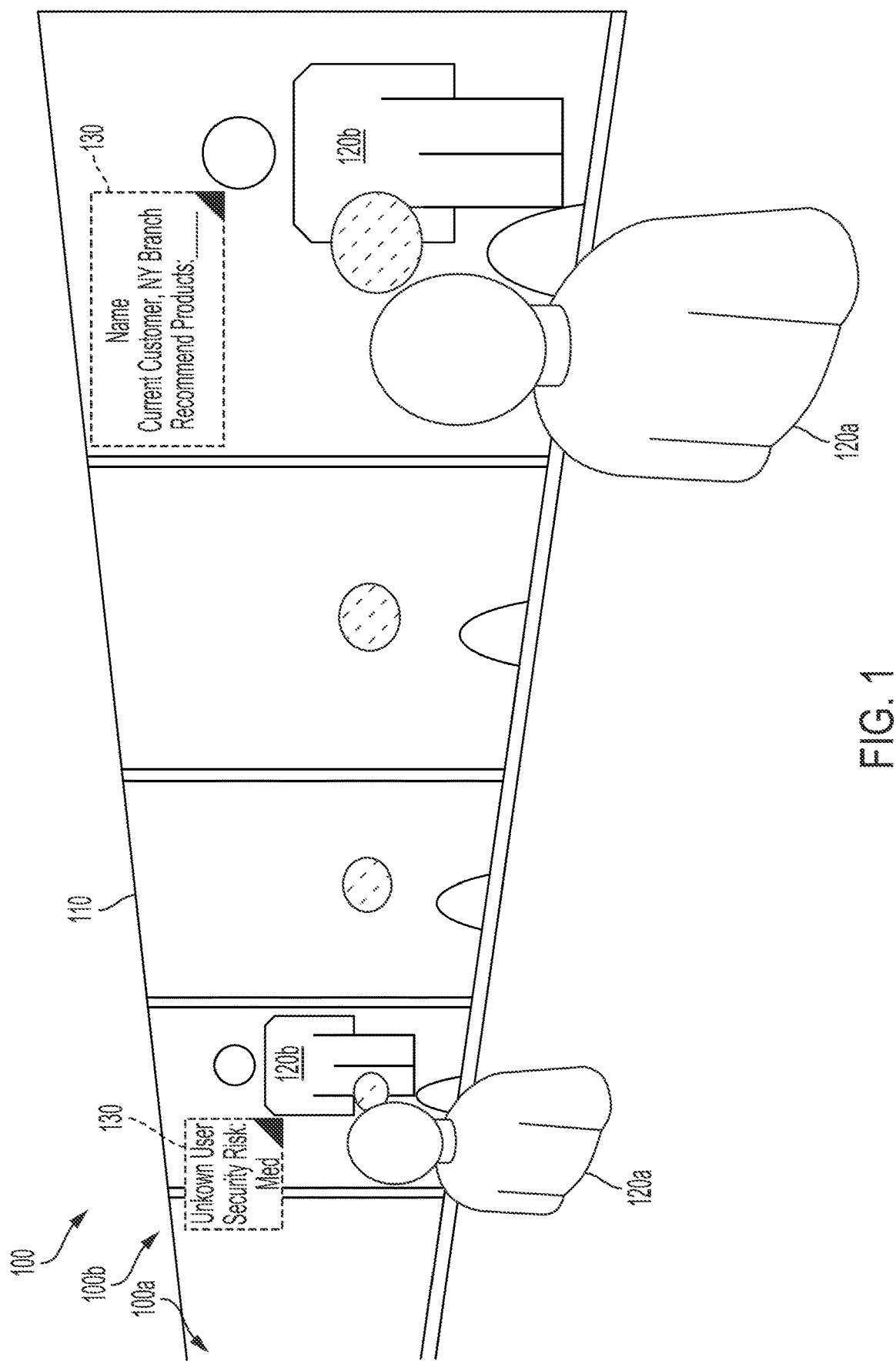
FIG. 1 is a diagram illustrating an example of a customer service environment according to some aspects of the present disclosure.

Certain aspects and features described herein relate to sensor-based user detection, identification, and authentication within customer service locations. In some embodiments, scanning systems including various sensor devices may be used at customer service locations to detect and identify users based on user-specific characteristics received via cameras and other scanning devices installed at the location. For example, a scanning system including one or more cameras and other scanning devices may be configured to monitor and capture sensor data from a location. In some implementations, a camera device may include a camera and the various sensor devices. Customer service locations may include locations such as banks or other financial institutions, as well as other retail locations (e.g., stores, restaurants, etc.), educational or governmental offices, and the like. In some embodiments, a scanning system may receive sensor data from its various scanning devices at the location, and may analyze the sensor data to detect a user at the location. For example, image data from cameras at the location, depth sensors, infrared sensors, door sensors, and various other sensors may be used to detect that a customer or other user has entered a particular location. Concurrently with or after detecting a user at the location, multiple user characteristics may be collected for the user, including visual characteristics, voice/audio characteristics, biometrics, and/or movement characteristics of the user. The user may be identified based on a combination of these user characteristics. In some cases, a data store may store combinations of user characteristics (e.g., visual, movement, biometric, etc.) associated with user profiles. After identifying a user to a threshold level of confidence, the corresponding user profile may be retrieved and used to determine one or more customer interaction strategies. Such customer interaction strategies may include recommendations of products or services, user-specific personality-based customer service techniques, or identification of potential threats of violence or fraud from customers. The customer interaction strategies then may be provided to a customer service representative to assist the representative in interacting with the customer.

At certain customer service locations, a transparent panel having one or more associated or integrated projector components may separate the customer area (e.g., bank lobby, product display areas, etc.) from the restricted areas at the location for which access is limited to the customer service representatives (e.g., employees). In such cases, an augmented reality customer interaction system may be implemented, including various cameras, location sensors, and the transparent panel including the associated projection components. In some embodiments, the augmented reality customer interaction system may receive image data captured via cameras directed to the customer side of the transparent panel. The individual users on the customer side of the transparent panel may be identified based on the image data and/or other sensor data received by the system (e.g., biometrics, user access codes, etc.), and associated user data may be retrieved for the identified users. For instance, the system may retrieve user account data, previous transactions, product or service recommendations, and the like. Customer interaction data such as a customer service script and/or product recommendations may be determined based on the retrieved user data, and the customer interaction data may be projected to the customer service representative side of the transparent panel. As discussed below in more detail, the customer interaction data may be projected so that is visible only on one side of the transparent panel (e.g., the customer service representative side) and is not visible to customers on the other side of the panel.

In some embodiments, projecting the customer interaction data may be performed using projectors integrated with the transparent panel. Additionally or alternatively, the data may be projected onto the panel from a separate projector, so that the data may be reflected by the panel and visible to the customer service representative. In various embodiments, the source from which the data is projected, the target location of the projection, and the angle of the projected data may be calculated based on the positions of the customer and customer service representative, so that the data appears next to the associated customer within the field of vision of the customer service representative. Thus, the projection of the customer interaction data at the appropriate place on the transparent panel provides an augmented reality user interface for the customer service representative, where the customer interaction data appears next to the associated customer from the perspective of the customer service representative.

Thus, the augmented reality customer interaction system may use cameras and sensors to determine and track both the locations of users on one side of the transparent panel (e.g., customers), and users on the other side of the transparent panel (e.g., customer service representatives). As users on both sides of the transparent panel move, the system may detect the movements and updated locations of the users, and then may update the projection of the customer interaction data so that it remains attached to the customer from the perspective of the customer service representative. In some cases, the system may allow customer service representatives to edit or update the interaction data for particular customers, and the updated data may remain associated with the customer while the customer remains at the location, including for the customer's interactions with other customer service representatives, and for subsequent visits by the customer to the same location or associated locations.

In the following description, for the purposes of explanation, specific details are set forth in order to provide a thorough understanding of various implementations and examples. Various implementations may be practiced without these specific details. For example, circuits, systems, algorithms, structures, techniques, networks, processes, and other components may be shown as components in block diagram form in order not to obscure the implementations in unnecessary detail. The figures and description are not intended to be restrictive.

In some examples, each process in the figures of this disclosure can be performed by one or more processing units. A processing unit may include one processor or multiple processors, including single core or multicore processors, one or more cores of processors, or combinations thereof. In some examples, a processing unit can include one or more special purpose co-processors such as graphics processors, Digital Signal Processors (DSPs), or the like. In some examples, some or all of the processing units can be implemented using customized circuits, such as Application Specific Integrated Circuits (ASICs), or Field programmable gate arrays (FPGAs). As used herein, reference to a processor may include one processor or more than one processor.

FIG. 1 is a diagram illustrating an example of a customer service environment 100 according to some aspects of the present disclosure. The customer service environment 100 may include a transparent panel 110 separating the users (e.g., customers) 120b in the customer area 100b from employees (e.g., customer service representatives) 120a in the employee area 100a. In some cases, the customer service environment 100 may be a bank or other financial institution, in which the bank employees (customer service representatives 120a) are separated from customers 120b by a secure transparent panel 110. In other cases, the customer service environment 100 may be a retail location, such as a store, gas station, or convenience store, or may be an administrative office, governmental office, educational office, etc. In this example, the transparent panel 110 functions as part of an augmented reality customer interaction system, in which customers 120b may be identified and customer-specific interaction data 130 may be projected onto (or from) a surface of the transparent panel 110 for viewing by the customer service representatives 120a.

Figure 2:
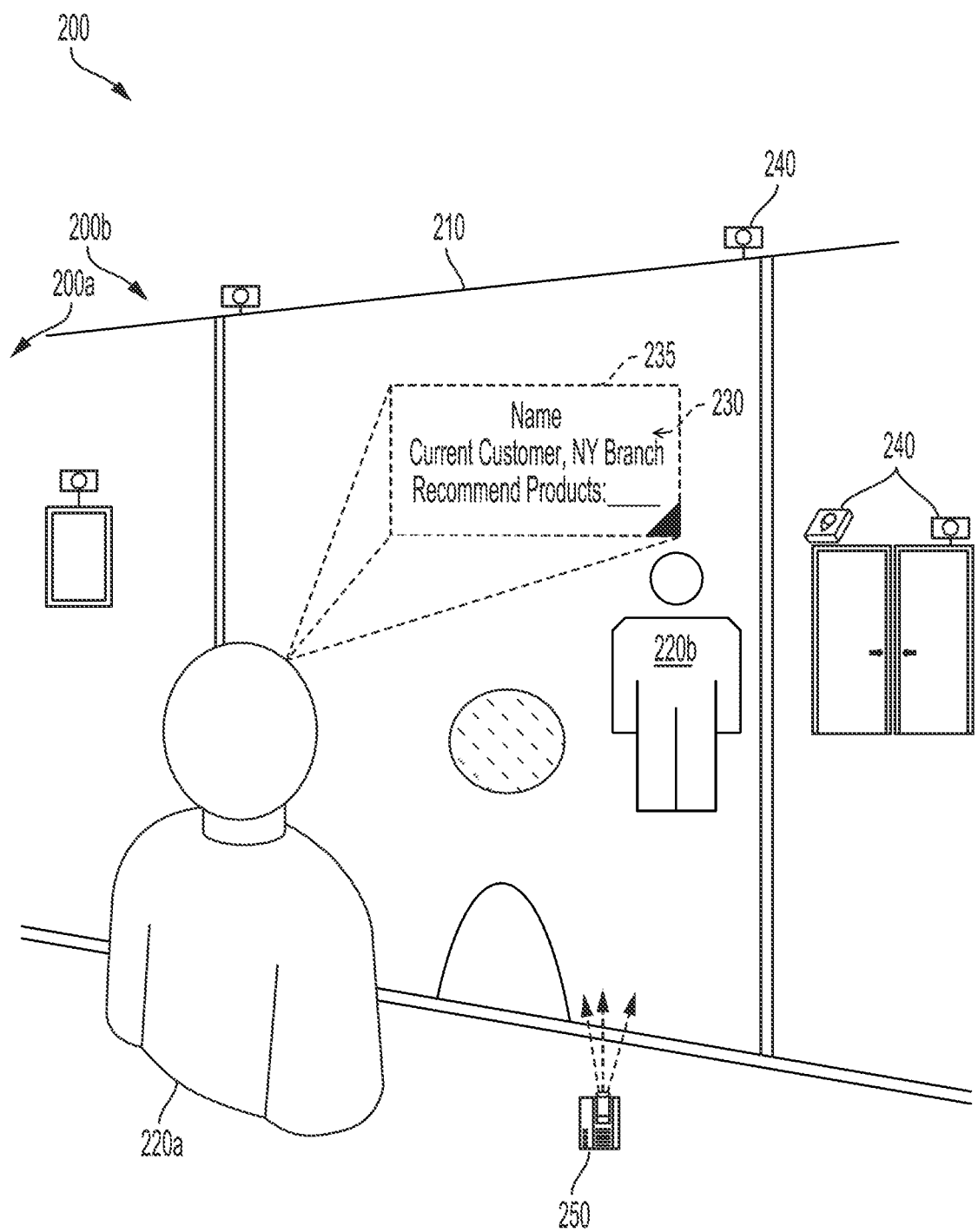
FIG. 2 is a diagram illustrating another example of a similar or identical customer service environment according to some aspects of the present disclosure.

FIG. 2 is a diagram illustrating another example of a similar or identical customer service environment at a location 200 according to some aspects of the present disclosure. The customer service environment at the location 200, may include a transparent panel 210 separating a customer service representative 220a on a restricted side 200a of the transparent panel 210 from a customer 220b on a customer side 200b of the transparent panel 210. As in the previous example, the identity of the customer 220b may be determined based on data gathered by a number of cameras and other sensors 240 installed at the customer service environment at the location 200, and one or more projection components 250 may be used to provide an augmented reality user interface that displays customer interaction data 230 specific to the customer 220b to the customer service representative 220a. The cameras and sensors 240 may include still image and video cameras, audio sensors, motion sensors (e.g., infrared sensors, depth sensors, etc.), biometric sensors (e.g., fingerprint scanners, retina or iris scanners, etc.), customer input devices (e.g., keypads and user interface terminals), customer device detectors (e.g., using NFC or Bluetooth to detect a known customer mobile device), and other sensors or detector devices capable of detecting characteristics of a customer 220b. As discussed below, in various examples the cameras and sensors 240 may be used for facial recognition analysis, ear recognition analysis, biometric analysis, gait analysis, user height/weight/size analysis, or to detect other identifying characteristics of customers 220b on the customer side 200b of the transparent panel 210. In some implementations, camera devices may include cameras, sensors, and detector devices. One or more projection components 250 may be integrated into the transparent panel 210, or may be configured to project images onto a surface of the transparent panel 210, to provide an augmented reality interface with customer interaction data 230 specific to the customer 220b that can be viewed by the customer service representative 220a.

In various embodiments, the customer interaction systems shown in FIG. 1 and FIG. 2 may be augmented reality systems, or "mixed reality" (or polyplexity) systems which merge real and virtual worlds. Transparent panel 210, which may be transparent or translucent, may be configured to allow for the injection of augmented reality elements 235 (e.g., floating windows) into the line-of-sight of customer service representatives 220a, without completely obscuring their view of the customer 220b or the customer side 200b of the customer service environment at the location 200. As discussed below, the projection of images within or onto the transparent panel 210 may be updated in response to movement by the customer 220b or employee ((customer service representative 220a), so that the employee (customer service representative 220a) may walk around and look at customer 220b from different distances and angles while the customer interaction data 230 remains "attached" to the customer 220b from the perspective of the employee (customer service representative 220a).

As shown in FIG. 2, a user scanning system and/or augmented reality customer interaction system may include a number of cameras and other sensors 240 facing out (or otherwise directed) into the customer side 200b of the location. Cameras and sensors 240 may be configured to scan the area and collect data from multiple angles. In some embodiments, the system may use the data collected by the location cameras and other sensors 240 to generate a digital model of the location, in order to determine the size, location, angles, and movement of the customer interaction data 230 to be displayed via the transparent panel 210. For instance, the augmented reality (or mixed reality) interface system may use a combination of standard video and infrared depth-sensing vision to draw a digital picture of the customer side 200b of the location 200.

In some embodiments, an augmented reality customer interaction system such as those shown in FIG. 1 and FIG. 2 also may determine the location of the customer service representative 220a, including position tracking as the customer service representative 220a moves on the restricted side 200a of the transparent panel 210. In some cases, cameras and other sensors 240 may be directed to the restricted side 200a of the transparent panel 210. The customer 220b and/or customer service representative 220a also may be outfitted with wearable devices (e.g., smartphones, smart watches, wearable computer glasses, etc.) in some cases, having motion-tracking sensors (e.g., accelerometer, gyroscope, magnetometer compass, etc.) to detect the precise position and movement of the users 220. Specifically, cameras and sensors 240 and/or other positioning techniques may provide advantages when used to determine the position/angle of the head and eyes of the customer service representative 220a, in order to allow the system to determine the position for the customer interaction data 230 on a surface of the transparent panel 210.

In some embodiments, the transparent panel 210 may be constructed using layers of colored glass to allow for the creation of graphical images that the customer service representatives 220a may interact with, or view from different angles. The transparent panel 210 also may be constructed as a passthrough device, so that customer service representatives 220a may view the real world through the transparent panel 210, while images (e.g., holograms) may be projected out in front of the customer service representative 220a.

In some cases, the transparent panel 210 of the augmented reality system may include integrated projectors that may be built directly into the transparent panel 210. For instance, such projectors may be implemented as using liquid crystal on silicon (LCoS) displays mounted on or near the transparent panel 210. These projectors may direct out images, which then pass through a combiner that combines the projected images and the real world. The transparent panel 210 may use total internal reflection (TIR) in some embodiments. TIR may, depending on the shape of the prism used, bounce light internally or aim light toward the eyes of the customer service representative 220a. Waveguides also may be used within the transparent panel 210, and/or a surface coating may be applied to allows the surface of the transparent panel 210 to create a series of diffraction gratings. For example, an image to be displayed may be transmitted through the optics of the transparent panel 210, coupled in through the diffraction grating, and diffracted inside the waveguide. The image then may be out-coupled. Different types of gratings may be used to make RGB color holograms, which may be implemented based on layered plates that form the transparent panel 210. Thus, the transparent panel 210 may project out an image to the customer service representative 220a, which then may be combined, diffracted and layered to produce images visible in space to the customer service representative 220a.

In various embodiments, for customer interaction systems using virtual reality, augmented reality, and/or mixed reality, the cameras and sensors 240 and corresponding positioning software may be used to perform head tracking, eye tracking, and depth sensing of the customer service representative 220a, as well as detailed room mapping both the restricted side 200a and customer side 200b of the transparent panel 210. Such cameras and sensors 240 may include cameras positioned at multiple angles, depth cameras; ambient light sensors, and/or photo/HD video cameras. Environmental sensing cameras may be included to provide the data for head tracking. A time of flight (ToF) depth camera may be included to serve two roles: to help with hand tracking in embodiments where the representative may use their hands to manipulate the customer interaction data 230 or other augmented reality elements, and also to perform surface reconstruction which may be used to place augmented reality elements on physical objects such as customers 220b.

As described above, projector components (e.g., liquid crystal projectors, combiners, diffraction gratings and waveguides) may be integrated into the transparent panel 210 to project image data directly to a customer service representative 220a. In other cases, externally positioned projection components 250 may be used, in conjunction with an angled and reflective surface, to project images that will be reflected back to the customer service representative 220a at the correct point within the representative's field of vision. The angle and/or layered composition of the transparent panel 210 may allow for the projected image to be visible on the restricted side 200a of the transparent panel 210 but not on the customer side 200b.

Figure 3:
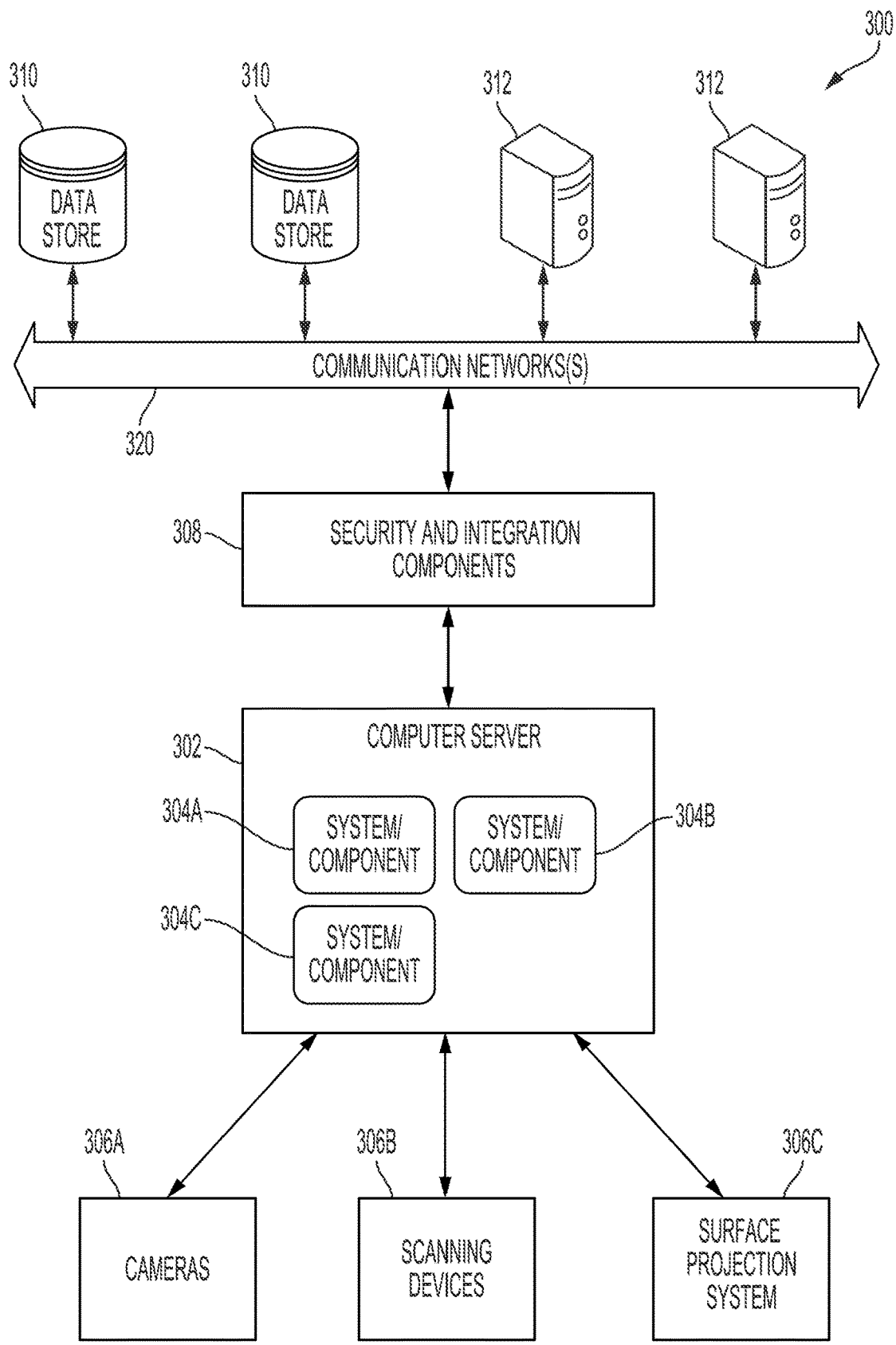
FIG. 3 is a diagram illustrating an example of a distributed computing environment according to some aspects of the present disclosure.

FIG. 3 is a diagram illustrating an example of a distributed computing environment 300 according to some aspects of the present disclosure. The distributed computing environment 300 may include a computer server 302, three front-end (or peripheral) computing devices (e.g., local cameras 306a, scanning devices 306b (e.g., sensors), and a surface projection system 306c), and other components that may implement certain embodiments and features described herein. In some embodiments, the server 302 and computing devices may operate at a customer service environment 100 or 200 (as shown in FIGS. 1 and 2, respectively) to implement a user scanning system or augmented reality customer interface system as described above. For example, server 302 may be a computer server operating a bank branch location, retail store location, administrative office location, etc. It may communicate with and control front-end peripheral devices such as local cameras 306a, scanning devices 306b (e.g., sensors), and a one-way surface projection system 306c to implement the user scanning capabilities and augmented reality customer user interface as described above.

Front-end peripheral devices 306a-306c may be, for example, off the shelf computing components configured to operate at a location 200, and communicate with and be controlled by server 302. Cameras 306a may capture image data at the location 200, scanning devices 306b may include various other sensors to capture additional data at the location 200, and surface projection system 306c may include a specialized surface and/or various projection components 250 configured to provide an augmented reality or mixed reality interface using the transparent panel 210. Server 302 may be communicatively coupled with the front-end peripheral devices 306a-306c via one or more communication networks. Front-end peripheral devices 306a-306c may receive client applications from server 302 or from other application providers (e.g., public or private application stores). Server 302 may be configured to run one or more server software applications or services, for example, web-based or cloud-based services, to support interaction with front-end peripheral devices 306a-306c. In some implementations, camera devices may include the sensors and the cameras.

Various different subsystems and/or components 304 may be implemented on server 302. The subsystems and components within the server 302 and front-end devices 306 may be implemented in hardware, firmware, software, or combinations thereof. Various different system configurations are possible in different distributed computing systems 300. Additionally, although exemplary computing environment 300 is shown with three front-end peripheral devices 306a-306c, any number of such devices may be supported. Other devices, such as specialized sensor devices, etc., may interact with front-end peripheral devices 306a-306c and/or server 302.

Computing environment 300 also may include one or more data stores 310 and/or back-end servers 312. For example, data stores 310 may store customer images and other characteristic data that may be used to identify customers detected at a location 200 based on the data collected by the front-end peripheral devices such as cameras 306a and scanning devices 306b (e.g., sensors). Data stores 310 also may store customer profiles, account data, previous customer interaction data, etc. Back-end servers 312 may include, for example, product recommendation engines, fraud/risk detection engines, etc., which may be used to generate the specific customer interaction data 230 once a customer has been identified. Data stores 310 and back-end servers 312 may reside in the same datacenter or may operate at a remote location from server 302. In some cases, one or more data stores 310 may reside on a non-transitory storage medium within the server 302. Other data stores 310 and back-end servers 312 may be remote from server 302 and configured to communicate with server 302 via one or more networks 320. In certain embodiments, data stores 310 and back-end servers 312 may reside in a storage-area network (SAN), or may use storage-as-a-service (STaaS) architectural model.

As shown, server 302 may use various security and integration components 308 to transmit, receive, and manage communications between the server 302 and the back-end data stores 310 and back-end severs 312. Although not shown in this example, server 302 also may use similar components and additional networks to communicate with and control the front-end peripheral devices 306a-306c, for example, when the server 302 is located remotely from the front-end peripheral devices 306a-306c. The security and integration components 308 may include separate servers, such as web servers and/or authentication servers, and/or specialized networking components, such as firewalls, routers, gateways, load balancers, and the like. For example, the security and integration components 308 may include one or more dedicated web servers and network hardware in a datacenter or a cloud infrastructure. In other examples, the security and integration components 308 may correspond to separate hardware and software components which may be operated at a separate physical location and/or by a separate entity.

Security and integration components 308 may implement various security features for data transmission and storage, such as authenticating users and restricting access to unknown or unauthorized users. In various implementations, security and integration components 308 may provide, for example, a file-based integration scheme or a service-based integration scheme for transmitting data between a particular location 200 (e.g., bank branch, retail location, office, etc.) and a centralized back-end datacenter and network of computing systems associated with the location 200. Security and integration components 308 may use secure data transmission protocols and/or encryption for data transfers, for example, File Transfer Protocol (FTP), Secure File Transfer Protocol (SFTP), and/or Pretty Good Privacy (PGP) encryption. In some embodiments, one or more web services may be implemented within the security and integration components 308, including cross-domain and/or cross-platform web services, which may be developed for enterprise use in accordance with various web service standards, such as RESTful web services (i.e., services based on the Representation State Transfer (REST) architectural style and constraints), and/or web services designed in accordance with the Web Service Interoperability (WS-I) guidelines. Some web services may use the Secure Sockets Layer (SSL) or Transport Layer Security (TLS) protocol to provide secure connections between the server 302 and back-end servers 312 or back-end data stores 310. SSL or TLS may use HTTP or HTTPS to provide authentication and confidentiality. In other examples, web services may be implemented using REST over HTTPS with the OAuth open standard for authentication, or using the WS-Security standard which provides for secure SOAP messages using XML encryption. In other examples, the security and integration components 308 may include specialized hardware for providing secure web services. For example, security and integration components 308 may include secure network appliances having built-in features such as hardware-accelerated SSL and HTTPS, WS-Security, and firewalls. Such specialized hardware may be installed and configured in front of any web servers, so that any external devices may communicate directly with the specialized hardware.

Communication network(s) 320 may be any type of network familiar to those skilled in the art that can support data communications using any of a variety of commercially-available protocols, including without limitation, TCP/IP (transmission control protocol/Internet protocol), SNA (systems network architecture), IPX (Internet packet exchange), Secure Sockets Layer (SSL) or Transport Layer Security (TLS) protocols, Hyper Text Transfer Protocol (HTTP) and Secure Hyper Text Transfer Protocol (HTTPS), Bluetooth®, Near Field Communication (NFC), and the like. Merely by way of example, network(s) 320 may be local area networks (LAN), such as one based on Ethernet, Token-Ring and/or the like. Network(s) 320 also may be wide-area networks, such as the Internet. Networks 320 may include telecommunication networks such as a public switched telephone networks (PSTNs), or virtual networks such as an intranet or an extranet. Infrared and wireless networks (e.g., using the Institute of Electrical and Electronics (IEEE) 802.11 protocol suite or other wireless protocols) also may be included in networks 320.

Figure 4:
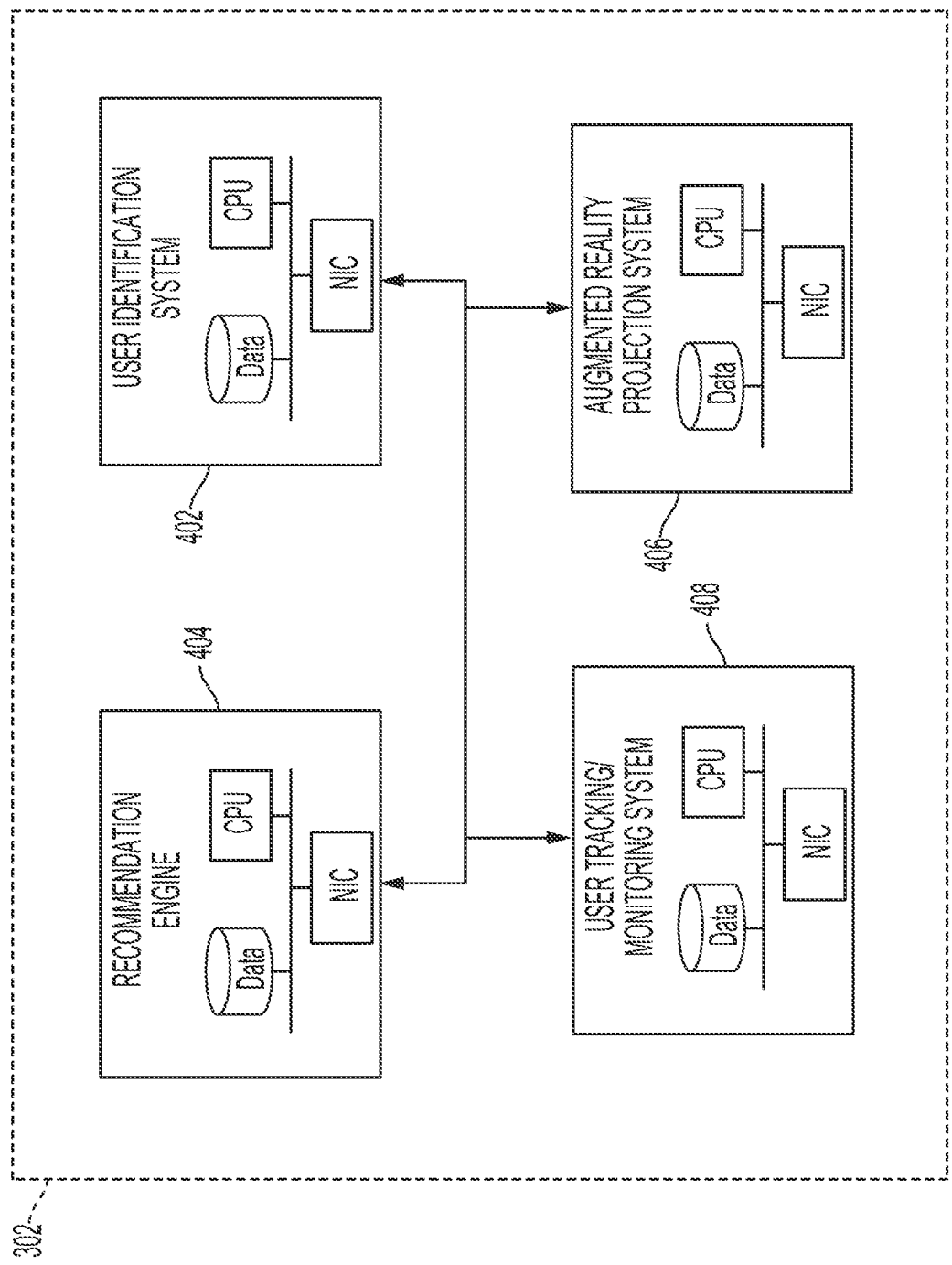
FIG. 4 is a block diagram illustrating an example embodiment of a computer server according to some aspects of the present disclosure.

FIG. 4 is a block diagram illustrating an example embodiment of a computer server 302 according to some aspects of the present disclosure. The computer server 302 may be used to implement the user scanning systems and/or augmented reality customer interface systems described herein. Server (s) 302 may include various server hardware and software components that manage the front-end devices 306, collect and analyze data from cameras 306a and scanning devices 306b, and provide interactive and adaptive content to users via one or more surface projection systems 306c.

For example, server 302 may include a user identification system 402. The user identification system 402 may be implemented using dedicated or shared hardware and software resources within the server 302. The user identification system 402 may be configured to request and retrieve image data and other sensor data from a location 200 at which users (e.g., customers) may be present. The user identification system 402 may dynamically control cameras 306a and other scanning devices 306b (e.g., movement sensors, biometric sensors, user interface systems, etc.) to collect user characteristics for a number of users present at the location 200. In some implementations, camera devices may include the sensors and the cameras. The user characteristic data may be analyzed and compared to previously stored user characteristic data to identify users as existing customers or other known individuals. In some cases, a combination of multiple different user characteristic data may be matched to previously stored data which may reside locally within the server 302 or remotely within a back-end system (e.g., data stores 310 or back-end servers 312). The user identification system 402 also may implement a confidence threshold for identifying users, and may control cameras 306a and scanning devices 306b to collect and process additional user characteristic data as the user moves around within the customer side 200b of the location 200, until reaching a minimum confidence threshold that the user can be positively identified. The confidence threshold may be based on the confidence of the individual matching factors (e.g., the confidence level of a particular facial recognition match), the reliability of the different types of user characteristic matching processes (e.g., fingerprint matching may be more reliable that facial recognition, which may be more reliable than gait recognition, etc.), and the number of different matching factors for which a positive user match was identified.

The server 302 also may include a recommendation engine 404. As described below, based on the user profiles and previous customer interactions for the users identified within the customer side 200b of the location 200, user-specific recommendations for customer interaction strategies may be determined by the recommendation engine 404. Such customer interaction strategies may include recommendations for products or services, customer communication preferences (e.g., languages), or recommendations based on customer personality traits or previous positive or negative interactions with the customer. The recommendation engine 404 may be implemented entirely at the server 302, or may communicate with back-end systems (e.g., data stores 310 or back-end servers 312) to retrieve and analyze the customer's account data, previous customer interactions, etc.

The server 302 also may include an augmented reality (or mixed reality) projection system 406. The augmented reality projection system 406 may be implemented using dedicated hardware at the location 200 (e.g., projection components 250 and transparent panel 210) as described above. After determining a recommendation for customer interaction strategy for a particular customer 220b, including an interaction script, recommendations, customer information, etc., the augmented reality projection system 406 may be configured to generate an augmented reality user interface for one or more customer service representatives 220a that may interact with the customer 220b. For instance, using projection components 250 and transparent panel 210, the augmented reality projection system 406 may generate and project customer interaction data to a particular location on a surface of the transparent panel 210 so that it may be visible to a customer service representative 220a and not to the customer 220b. The projection system 406 may, for example, determine and track the positions of the customer service representative 220a and the customer 220b, and may project the customer interaction data 230 to a position on the transparent panel 210 so that the customer interaction data 230 will be associated with the customer 220b from the visual perspective of the customer service representative 220a. For example, the customer interaction data 230 may be attached to the customer 220b from the perspective of the customer service representative 220a, and the projection system 406 may move the customer interaction data 230 as needed to maintain the attachment of the augmented reality data to the customer 220b as both the customer 220b and the customer service representative 220a may move around on their respective sides of the transparent panel 210.

The server 302 also may include a user tracking and monitoring system 408. The user tracking and monitoring system 408 may track the locations of multiple customers 220b and multiple customer service representatives 220a at the location, in order to assign specific customers to specific representatives and manage the overall customer experience at the location 200. For example, in scenarios where multiple customers 220b at the location 200 and/or multiple customer service representatives 220a are available to interact with the customers 220b, the user tracking and monitoring system 408 may determine a preferred customer service representative 220a to interact with a particular customer 220b. Such determinations may be based on customer language preferences (e.g., a Spanish-speaking customer may be routed to particular representative fluent in Spanish), customer account type/details (e.g., a customer with a large or complex account portfolio may be routed to a senior service representative), or customer temperament (e.g., a difficult customer with a history of negative interactions may be routed to a manager), and so on. Such routing may be performed by means of the projection system 406. For example, the customer interaction data 230 for a customer 220b may be projected so that it is visible to the preferred customer service representative 220a for that customer.

The user tracking and monitoring system 408 also may allow customer service representatives 220a to update the customer interaction data 230 during the customer's visit to the location 200. For instance, if a customer 220b interacts with a first customer service representative 220a to request certain information or attempt to perform a certain type of purchase or transaction, the first customer service representative 220a may update the customer interaction data 230 for that customer 220b to indicate the customer's purpose at the location 200, the customer's current mood, and/or other customer information. Then, if the same customer 220b interacts with a different customer service representative 220a during the same visit to the location, or during a subsequent visit to the same or different related location, then the customer interaction data 230 for that customer 220b may automatically include the customer's purpose, questions, mood, or any other customer information input by the first customer service representative, which may benefit the second customer service representative 220a in assisting the customer 220b.

Figure 5:
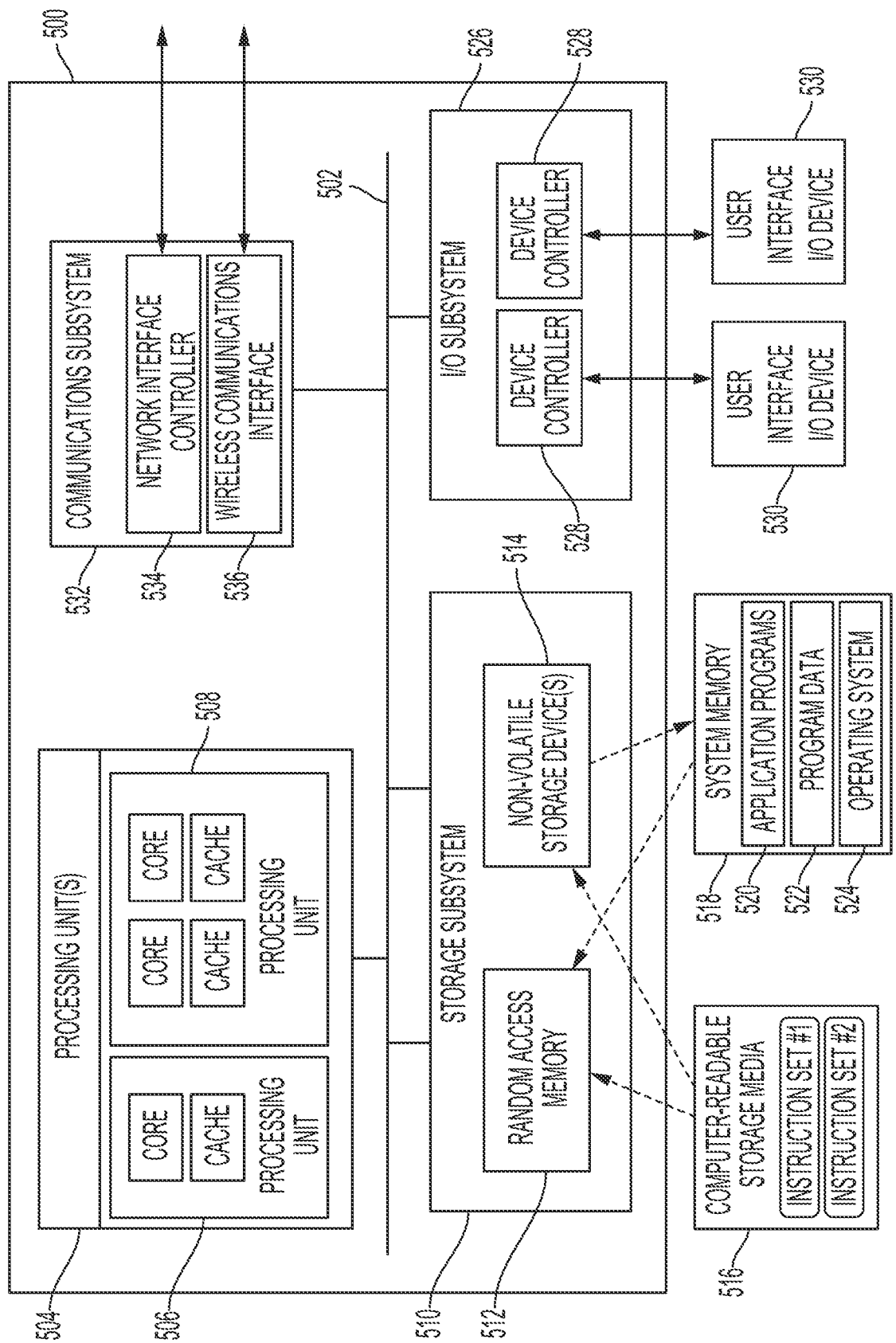
FIG. 5 is a block diagram of an illustrative computer system according to some aspects of the present disclosure.

FIG. 5 is a block diagram of an illustrative computer system 500 according to some aspects of the present disclosure. The computer system 500 may correspond to the computer server 302, front-end peripheral devices 306a-306c, or any other of the computing devices or servers described herein. In this example, computer system 500 includes processing units 504 that communicate with a number of peripheral subsystems via a bus subsystem 502. These peripheral subsystems include, for example, a storage subsystem 510, an I/O subsystem 526, and a communications subsystem 532.

Bus subsystem 502 provides a mechanism for enabling the various components and subsystems of computer system 500 to communicate with each other. Although bus subsystem 502 is shown schematically as a single bus, alternative embodiments of the bus subsystem may utilize multiple buses. Bus subsystem 502 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 504, which may be implemented as one or more integrated circuits (e.g., a conventional microprocessor or microcontroller), controls the operation of computer system 500. One or more processors, including single core and/or multicore processors, may be included in processing unit 504. As shown in the figure, processing unit 504 may be implemented as one or more independent processing units 506 and/or 508 with single or multicore processors and processor caches included in each processing unit. In other embodiments, processing unit 504 may also be implemented as a quad-core processing unit or larger multicore designs (e.g., hexa-core processors, octo-core processors, ten-core processors, or greater.

Processing unit 504 may execute a variety of software processes embodied in program code (e.g., such as software processes corresponding to systems 402-408), and may maintain multiple concurrently executing programs or processes. At any given time, some or all of the program code to be executed can be resident in processing unit(s) 504 and/or in storage subsystem 510. In some embodiments, computer system 500 may include one or more specialized processors, such as digital signal processors (DSPs), outboard processors, graphics processors, application-specific processors, and/or the like.

Input/Output (I/O) subsystem 526 may include device controllers 528 for one or more user interface input devices and/or user interface output devices 530. User interface input and output devices 530 may be integral with the computer system 500 (e.g., integrated audio/video systems, and/or touchscreen displays), or may be separate peripheral devices which are attachable/detachable from the computer system 500.

Input devices of the user I/O devices 530 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices of the user I/O devices 530 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode readers, 3D scanners, 3D printers, laser rangefinders, and eye gaze tracking devices. Additional input devices of the user I/O devices 530 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices of the user I/O devices 530 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, and the like. In general, use of the term "output device" is intended to include all possible types of devices and mechanisms for outputting information from computer system 500 to a user or other computer. For example, output devices of the user I/O devices 530 may include, without limitation, a variety of display devices that visually convey text, graphics and audio/video information such as monitors, printers, speakers, headphones, automotive navigation systems, plotters, voice output devices, and modems.

Computer system 500 may comprise one or more storage subsystems 510, comprising hardware and software components used for storing data and program instructions, such as system memory 518 and computer-readable storage media 516. The system memory 518 and/or computer-readable storage media 516 may store program instructions that are loadable and executable on processing units 504, as well as data generated during the execution of these programs.

Depending on the configuration and type of computer system 500, system memory 318 may be stored in volatile memory (such as random access memory (RAM) 512) and/or in non-volatile storage drives 514 (such as read-only memory (ROM), flash memory, etc.) The RAM 512 may contain data and/or program modules that are immediately accessible to and/or presently being operated and executed by processing units 504. In some implementations, system memory 518 may include multiple different types of memory, such as static random access memory (SRAM) or dynamic random access memory (DRAM). In some implementations, a basic input/output system (BIOS), containing the basic routines that help to transfer information between elements within computer system 500, such as during start-up, may typically be stored in the non-volatile storage drives 514. By way of example, and not limitation, system memory 518 may include application programs 520, such as client applications, Web browsers, mid-tier applications, server applications, etc., program data 522, and an operating system 524.

Storage subsystem 510 also may provide one or more tangible computer-readable storage media 516 for storing the basic programming and data constructs that provide the functionality of some embodiments. Software (programs, code modules, instructions) that when executed by a processor provide the functionality described herein may be stored in storage subsystem 510. These software modules or instructions may be executed by processing units 504. Storage subsystem 510 may also provide a repository for storing data.

Storage subsystem 510 may also include a computer-readable storage media reader (not shown) that can be connected to computer-readable storage media 516. Together and, optionally, in combination with system memory 518, computer-readable storage media 516 may comprehensively represent remote, local, fixed, and/or removable storage devices plus storage media for temporarily and/or more permanently containing, storing, transmitting, and retrieving computer-readable information.

Computer-readable storage media 516 containing program code, or portions of program code, may include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 500.

By way of example, computer-readable storage media 516 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 516 may include, but is not limited to, Zip® drives, flash memory cards, universal serial bus (USB) flash drives, secure digital (SD) cards, DVD disks, digital video tape, and the like. Computer-readable storage media 516 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 500.

Communications subsystem 532 may provide a communication interface from computer system 500 and external computing devices via one or more communication networks, including local area networks (LANs), wide area networks (WANs) (e.g., the Internet), and various wireless telecommunications networks. As illustrated in FIG. 5, the communications subsystem 532 may include, for example, one or more network interface controllers (NICs) 534, such as Ethernet cards, Asynchronous Transfer Mode NICs, Token Ring NICs, and the like, as well as one or more wireless communications interfaces 536, such as wireless network interface controllers (WNICs), wireless network adapters, and the like. Additionally and/or alternatively, the communications subsystem 532 may include one or more modems (telephone, satellite, cable, ISDN), synchronous or asynchronous digital subscriber line (DSL) units, FireWire® interfaces, USB® interfaces, and the like. Communications subsystem 536 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

The various physical components of the communications subsystem 532 may be detachable components coupled to the computer system 500 via a computer network, a Fire-Wire® bus, or the like, and/or may be physically integrated onto a motherboard of the computer system 500. Communications subsystem 532 also may be implemented in whole or in part by software.

In some embodiments, communications subsystem 532 may also receive input communication in the form of structured and/or unstructured data feeds, event streams, event updates, and the like, on behalf of one or more users who may use or access computer system 500. For example, communications subsystem 532 may be configured to receive data feeds in real-time from users of social networks and/or other communication services, web feeds such as Rich Site Summary (RSS) feeds, and/or real-time updates from one or more third party information sources (e.g., data aggregators 309). Additionally, communications subsystem 532 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 532 may output such structured and/or unstructured data feeds, event streams, event updates, and the like to one or more data stores 104 that may be in communication with one or more streaming data source computers coupled to computer system 500.

Due to the ever-changing nature of computers and networks, the description of computer system 500 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 6:
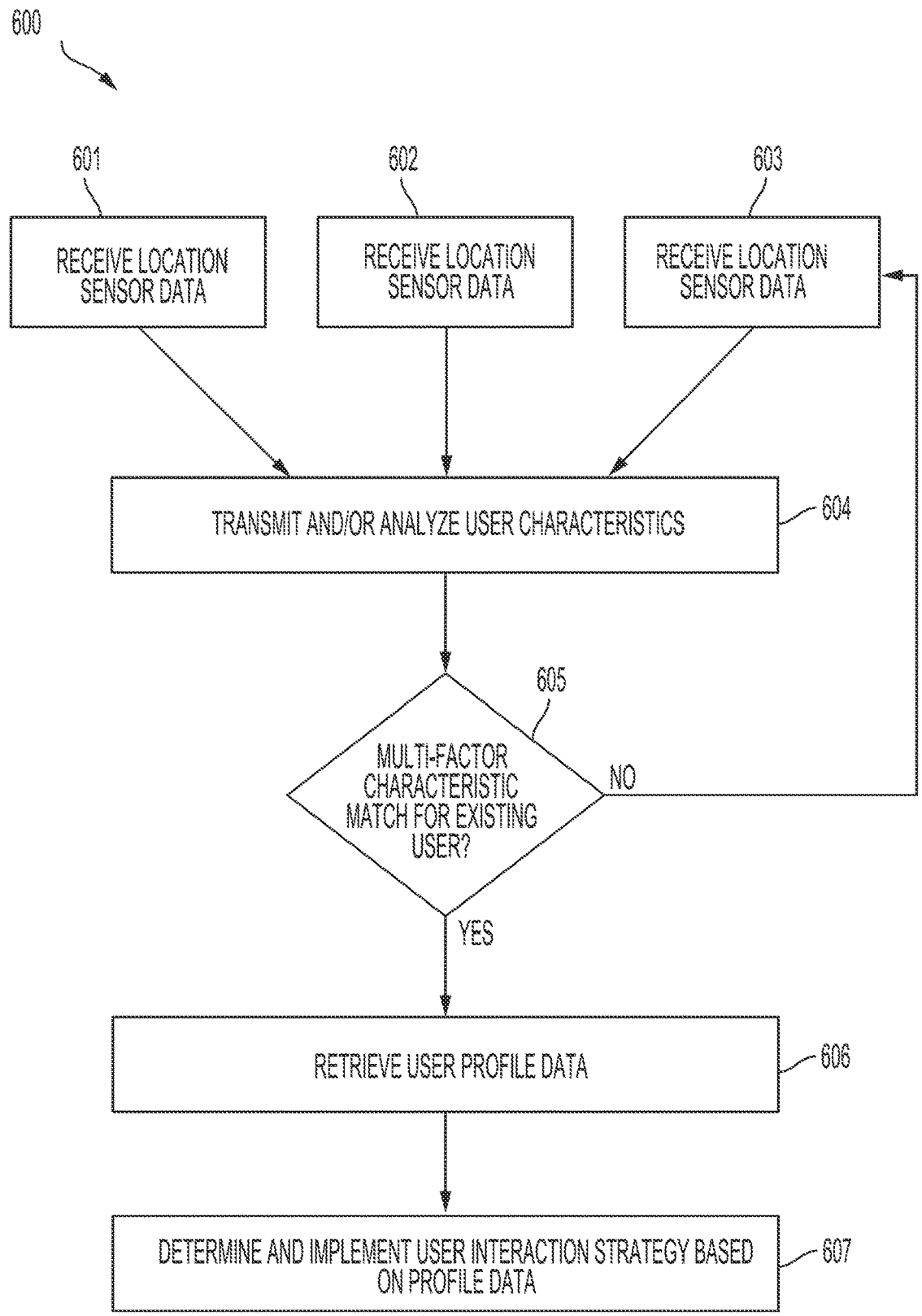
FIG. 6 is a flowchart illustrating an example of a process for identifying a user at a location based on multiple sensors and multi-factor user characteristic matching according to some aspects of the present disclosure.

FIG. 6 is a flowchart illustrating an example of a process 600 for identifying a user at a location based on multiple sensors and multi-factor user characteristic matching according to some aspects of the present disclosure. As described below, the techniques in FIG. 6 may be used to detect and identify a customer 220*b* within a location 200, such as a bank, retail location, office, etc. Multiple different sensors, detectors, and location scanning devices may be used to identify various characteristics of the user, including visual characteristics, biometric characteristics, movement characteristics, and other characteristics of the user. In some implementations, camera devices may include the sensors and the cameras. The data from multiple sensor devices may be synchronized for time and location to determine multiple different characteristics of a single user within the location. A particular customer or other known user may be identified based on a multi-factor matching. Multi-factor matching is matching of multiple different characteristics of the same user. Based on the identification of the existing customer or other known user within a confidence threshold, a user profile or other user data may be retrieved and an interaction strategy may be determined for handling customer service or other interactions with the user.

In blocks 601-603, the server 302 may receive location sensor data from various different sensor devices. Although blocks 601-603 describe that sensor data may be received from three different sensor devices, in various examples sensor data may be received from any number of cameras 306*a* or other scanning devices 306*b* (e.g., sensors). The sensor data received in blocks 601-603 may include image or streams of video data from multiple cameras 306*a* operating on the customer side 200*b* of a location 200. The image or video data captured from cameras 306*a* may be used for facial recognition analysis, ear recognition analysis, user size height or size analysis, gait or movement analysis, and the like. Different cameras 306*a* may be positioned differently within the location 200 to capture image or video data of users from different heights and at different angles.

In addition to image and video data received from cameras 306*a*, various other data may be received from scanning devices 306*b* in blocks 601-603. Such sensor data may include biometric data collected from the users on the customer side 200*b* of a location 200. Examples of biometric data that may be collected may include fingerprint data from a fingerprint scanner at the location 200, voice data from one or more microphones at the location 200, retina or iris scans from scanners at the location 200, signature data collected from the user at the location, and so on. In some implementations, camera devices may include the sensors and the cameras.

In some embodiments, scanning devices 306*b* may include devices configured to detect and identify one or more mobile devices worn by or carried by users within the location, such as smartphones, smart watches, computer glasses, etc. Scanning devices 306*b* may automatically communicate with the customer's mobile devices via a wireless protocol such as Bluetooth or NFC, to identify a device name, device type, MAC address, or other identifying information of the device. Such device identifying information may be used in conjunction with user image data and/or other sensor data to identify a customer or other known user.

Additionally, scanning devices 306*b* at the location may include user terminals, keypads, card readers, or other devices configured to interact with the user. For example, in certain secure locations 200, users may be required to insert a card or scan a fob or other identification data before they are permitted access to the location 200. In other examples, a user at the location may optionally interact with a check-in kiosk or terminal, or may be required to interact with such a kiosk or terminal, to provide their name or other identifying information and the purpose of their visit. This additional user-identifying information also may be used in conjunction with user image data and/or other sensor data to identify customers or other known users at the location.

In block 604, the server 302 may analyze the data received from the cameras 306*a* and scanning devices 306*b*, to determine and isolate the particular characteristics of users at the location 200. In some cases, the server 302 may preprocess and transmit sensor data (e.g., facial images, biometric data, etc.) to one or more backend systems 310-312 to determine whether or not the received data matches a known user. Additionally or alternatively, the server 302 may analyze the image and sensor data locally, and compare the data to locally stored user characteristic data (e.g., frequent customers or visitors to a location 200, such as a specific branch location), to identify a user matching the image data and/or sensor data.

The analysis performed in block 604 may include initially synchronizing the image data and sensor data from multiple cameras 306*a* and scanning devices 306*b*, with respect to time and user position on the customer side 200*b* of the location 200. As noted above, the customer side 200*b* of the location 200 may include multiple different customers at once. Additionally, the different customers at the location 200 may enter and leave the location 200 periodically, and may move around and mingle with other customers in the location 200. Thus, the server 302 may be configured to synchronize the image and sensor data from multiple cameras 306*a* and scanning devices 306*b*, so that data from multiple sources can be collected and evaluated for a single user. The cameras 306*a* and scanning devices 306*b* detecting the user data, as well as the server 302 receiving and processing the user data, also may be configured to distinguish between different users in the location 200, to track individual users and they move around within the customer side 200*b* of the location 200, and to retain user characteristic data to match customers as they exit and re-enter the location 200.

Figure 7A:
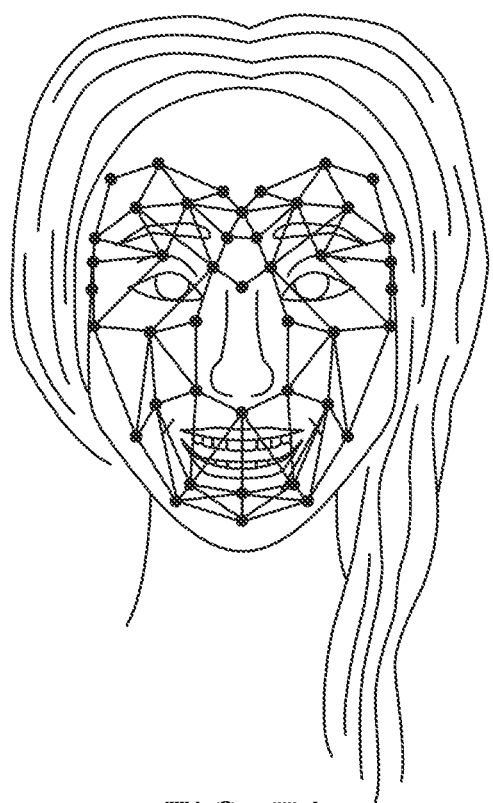
FIGS. 7A and 7B illustrate examples of collecting visual facial and ear recognition data according to aspects of the present disclosure.
Figure 7B:
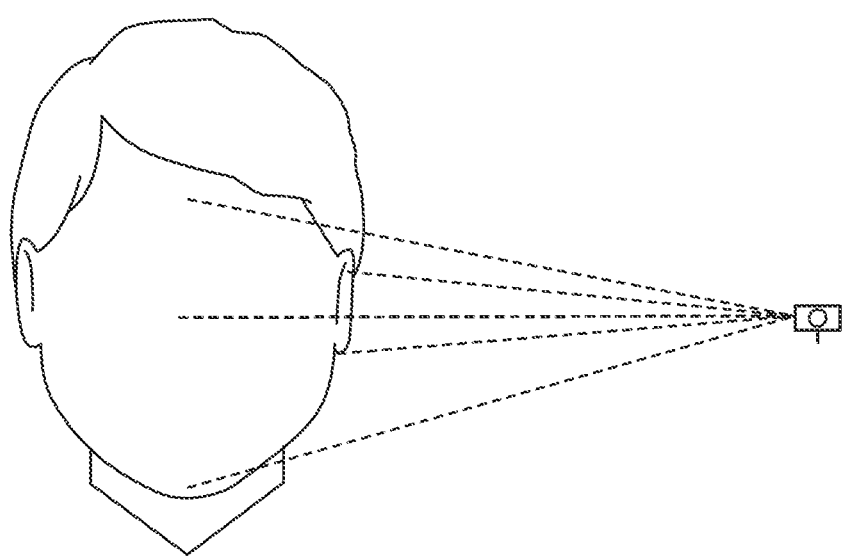

After time synchronizing and position synchronizing the data received in blocks 601-603 to isolate a single user within the location 200, at block 604, analysis of the data may be performed. The analysis performed in block 604 may include various different types of user identification analyses. For instance, the server 302 may perform (e.g., individually or via requests to back-end servers 312 and back-end data stores 310) facial recognition analysis, ear recognition analysis, biometric analysis, voiceprint analysis, written signature analysis, gait analysis, user height/weight/size analysis, among other user identification techniques described herein. FIGS. 7A and 7B illustrate examples of collecting visual facial and ear recognition data according to aspects of the present disclosure. Referring to FIG. 7A visual facial recognition data may be collected on a first user via a first set of cameras 306*a*. As shown in FIG. 7B, ear recognition data may be collected on a second user via a second set of cameras 306*a* operating at the location 200. In some implementations, both facial recognition and ear recognition may be performed on the same user.

Referring again to FIG. 6, in block 605, the server 302 may perform a multi-factor user characteristic match to determine if a customer or other known user may be identified based on the combination of the image data and/or sensor data. As noted above, a multi-factor user characteristic matching process may include matching multiple different characteristics of a single user received from different cameras 306*a* and/or scanning devices 306*b* at the location 200. Multi-factor user characteristic matching may be used in some implementations, and may provide advantages of additional user authentication and security to prevent misidentification of a user by a single system, for example, misidentification of a bad actor attempting to impersonate a different user. In some embodiments, the server 302 may implement a two-factor user characteristic matching process in which different user identification matches may be required to sufficiently identify a user in block 605. A two-factor user characteristic matching process may include, for example, a positive facial recognition match with a user and a positive ear recognition match with the same user. In various other examples, a two-factor user characteristic matching process may include any combination of facial recognition, ear recognition, gait recognition, user size/shape matching, fingerprint matching, voice analysis matching, retinal or iris scan matching, and/or any combination of positive matches of the various user characteristics and sensor data described herein. In certain embodiments, the server 302 may implement a three-factor user characteristic matching process in which three separate user characteristic matches may be independent determined, or a four-factor process, a five-factor process, and so on.

If an existing customer or other known user is identified based on the multi-factor user characteristic matching process in block 605, then in block 606 the server 302 may retrieve a user profile and additional user data for the identified user. For instance, the server 302 may request and receive the users account data, profile data, current account balances, previous purchases or transaction history data, and the like, from back-end systems (e.g., data stores 310 and back-end servers 312). In block 607, the server 302 may determine a user interaction strategy based on the user data retrieved in block 606. The user interaction strategy recommendations may provide products or services for the customer, user-specific customer language preferences, user-specific personality-based customer service techniques, and/or identification of potential threats of violence or fraud from the user. As discussed below, the user interaction strategies may be provided to the appropriate customer service representative 220*a* to assist the representative in interacting with the customer 220*b*.

In some embodiments, if an existing customer or other known user cannot be identified based on the multi-factor user characteristic matching process in block 605, then the server 302 may continue monitoring the user within the location using the same sets of cameras 306*a* and scanning devices 306*b*, and/or additional front-end peripheral devices until the identity of the user can be determined. For instance, the server 302 may be initially unable to identify a user that recently entered a location 200 such as bank branch or retail store. However, as the user moves spends more time in the location 200, moves around the location, and interacts with people or devices at the location 200, additional image and sensor data may be collected for the user and a subsequent multi-factor user characteristic matching process may be successful to identify the user. In some cases, an overall confidence threshold may be implemented in block 605, where the overall confidence of the multi-factor match may be based on the confidence of the individual matching factors (e.g., the confidence level of a particular facial recognition match), the reliability of the different types of user characteristic matching processes (e.g., fingerprint matching may be more reliable that facial recognition, which may be more reliable than gait recognition, etc.), and the number of different matching factors for which a positive user match was identified.

The specific operations illustrated in FIG. 6 provide a particular process for identifying a user at a location based on multiple sensors and multi-factor user characteristic matching according to an embodiment. Other sequences of operations may also be performed according to alternative embodiments. For example, alternative embodiments may perform the operations outlined above in a different order. Moreover, the individual operations illustrated in FIG. 6 may include multiple sub-operations that may be performed in various sequences as appropriate to the individual operations. Furthermore, additional operations may be added or removed depending on the particular applications.

Figure 8:
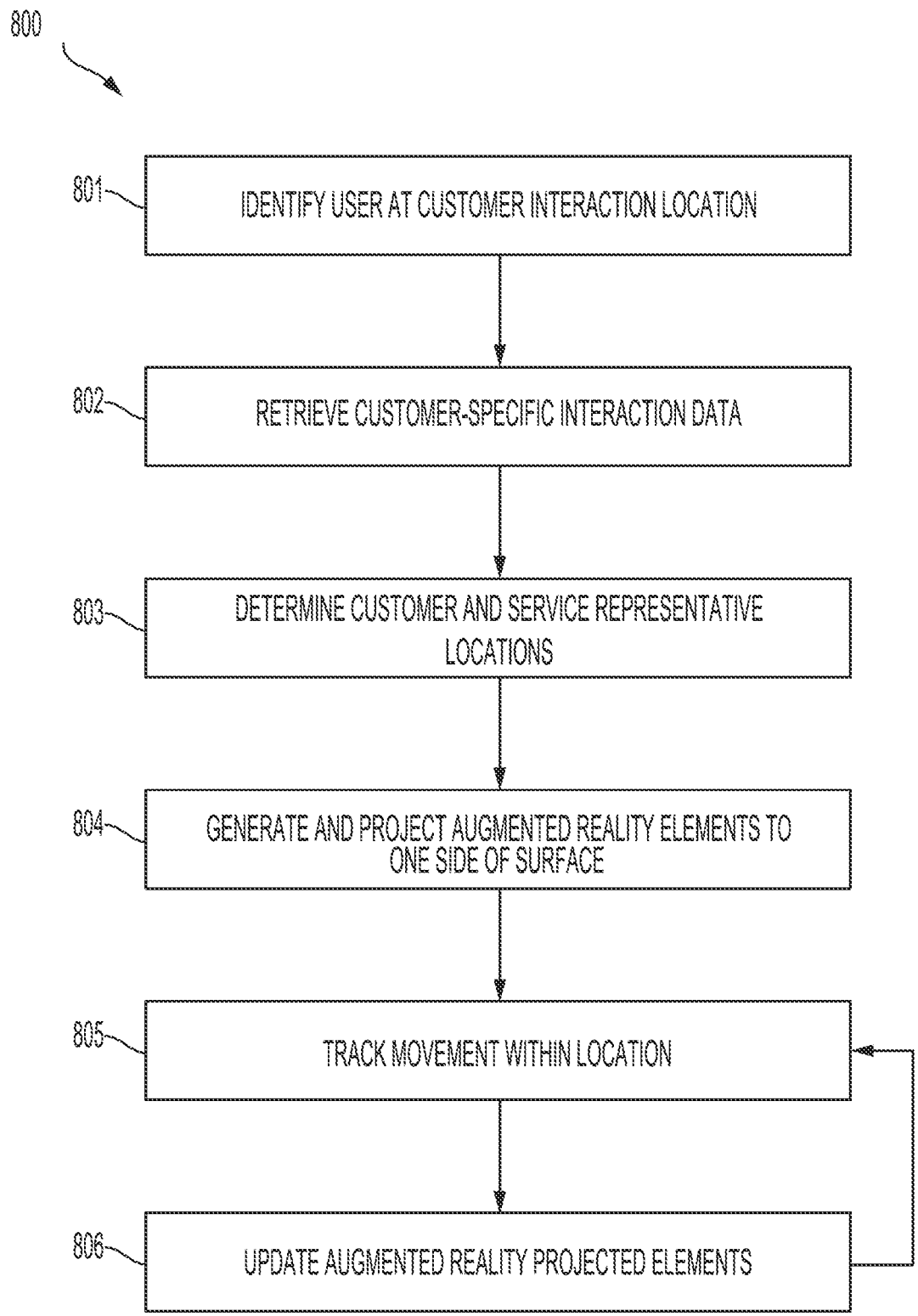
FIG. 8 is a flowchart illustrating an example of a process for generating and providing augmented reality content (and/or mixed reality content) to one side of a transparent panel according to aspects of the present disclosure.

FIG. 8 is a flowchart illustrating an example of a process 800 for generating and providing augmented reality content (and/or mixed reality content) to one side of a transparent panel. The augmented reality content (and/or mixed reality content) may be generated to one side of a transparent panel in order to implement a customer interaction strategy. As described below, the techniques in FIG. 8 may be used to provide a customer service representative 220*a* with customer interaction data 230 specific to the customer 220*b* that may assist the customer service representative 220*a* in interacting with the customer 220*b*. The customer interaction data 230 may be provided using a projection system including projection components 250 and a transparent panel 210 in such a way that the customer interaction data 230 may be attached to the customer 220b from the visual perspective of the customer service representative 220a, but also in a way so that it is not visible to the customer 220b. As described below, such augmented reality techniques may allow customer service representatives 220a to be provided with customer information, customer interaction scripts, suggestions for product or service recommendations, conflict resolution strategies, and other data to allow the customer service representatives 220a to more effectively interact with customers 220b.

In block 801, a user may be identified at a customer interaction location. As described above, the customer interaction location 200 may include a bank, retail location, administrative office, or any location monitored by one or more cameras 306a or scanning devices 306b. The identification of the user may be based on the cameras 306a and scanning devices 306b, using the various techniques described above in FIG. 6. In other examples, the identification of the user in block 801 may be based on a user data received via a sign-in terminal or kiosk, or based on the credentials provided by the user to access the location 200.

As described above, the customer interaction location may correspond to customer service locations at which one or more customer service representatives 220a may interact with customers 220b or other users. In some embodiments, such locations 200 may include a transparent panel 210 that separates a customer area on the customer side 200b of the transparent panel 210 (e.g., bank lobby, product display areas, etc.) from a restricted area on the restricted side 200a of the transparent panel 210 for which access is limited to employees or customer service representatives. The transparent panel 210 may be part of an augmented reality projection system, in which projection components 250 may be used to project data onto the transparent panel which may be viewable only from the area on the restricted side 200a of the transparent panel 210.

In block 802, the server 302 may retrieve customer interaction data based on the user identified in block 801. In some cases, the customer interaction data may include customer data (e.g., the customer's name, account types, account balances, home city or home branch location, and/or customer personal data), to allow the customer service representative 220a to interact more readily with the customer 220b. Additionally or alternatively, the customer interaction data may include customer language preferences, produce or service recommendations, the results of data analysis regarding the customer's likely purpose of the visit, or customer management or conflict resolution strategies for interacting with the customer based on previous interactions with the same customer.

In block 803, the server 302 may determine the current positions of one or both of the customer 220b for which the customer interaction data was retrieved in block 802, and a customer service representative 220a that may interact with that customer 220b. In some cases, a customer service representative 220a may be selected from multiple possible customer service representatives 220a that may be available to interact with the customer 220b. For instance, a particular customer service representative 220a on the restricted side 200a of the transparent panel 210 may be selected based on proximity to the customer 220b, current availability of the customer service representative 220a, language compatibility between the customer service representative 220a and customer 220b, personality compatibility between the customer service representative 220a and customer 220b, compatibility between the qualifications or expertise of the customer service representative 220a and likely requests of the customer 220b, or any combination of these factors.

After selecting a particular customer service representative 220a to interact with the customer 220b, the server 302 may determine a current location of the customer service representative 220a and/or the customer 220b in order to position the graphical elements of the augmented reality user interface. In some embodiments, the server 302 may assume the position the customer service representative 220a and/or the customer 220b based on the position of a customer service window, the location of speaking hole at the window, the layout of the desks or countertops at which the parties are sitting or standing, etc. In other embodiments, both the positions of the customer service representative 220a and/or the customer 220b may be determined in block 803 based on cameras 306a and scanning devices 306b operating at the location 200. For example, cameras 306a and scanning devices 306b directed to the restricted area on the restricted side 200a of the transparent panel 210 may be used to detect the position and height of the customer service representative 220a, and may perform head tracking, eye tracking, and depth sensing for precise positioning of the customer service representative 220a. Additional cameras 306a and scanning devices 306b directed to the customer side 200b of the location 200 may be used to track the current position, posture, and movement of the customer 220b within the location 200.

In block 804, the server 302 may generate the augmented reality content and engage the transparent panel 210 and/or projection components 250 to project the augmented reality content to be visible to the customer service representative 220a. The augmented reality content generated in block 804 may be based on user-specific customer interaction data retrieved in block 802. As discussed above, the data may include a customer data, a customer service script, product or service recommendations, and other customer-specific information. In block 804, the server 302 may determine the size and positioning of one or more augmented reality elements to contain some or all of the customer interaction data. In some embodiments, the size and positioning of augmented reality elements 235 may be determined so that the elements appear near (or attached to) the associated customer 220b when viewed from the perspective of the customer service representative 220a. Thus, multiple different augmented reality elements may be generated and projected to the customer service representative 220a, where different elements may be associated with and may appear near or attached to different customers 220b in the location 200. In some cases, the server 302 also may select the sizes and positions of the augmented reality elements so as not to obscure the associated customer 220b or the faces of other users on the customer side 200b of the location 200, from the visual perspective of the customer service representative 220a.

Referring to the example shown in FIG. 2, the augmented reality element 235 is shown as a text box projected from the transparent panel 210 to appear as a floating window above the associated customer 220b. Such types of augmented reality elements 235 may contain customer information, scripts, recommendations, and other customer-specific information. However, it should be understood that in other examples, any number of different types of augmented reality elements may be used. For instance, different customers 220b may be labeled and/or color-coded using augmented reality elements to identify known and unknown customers, or based on account types and balances, arrival times and wait times at the location 200, etc. In some cases, customers 220b that may be identified as potential fraudsters or may represent potential threats of violence may be especially highlighted to all of the customer service representatives 220a. Additionally, in such cases, the augmented reality elements projected to the customer service representatives 220a may include images or video feeds showing the customer 220b from different angles to allow the customer service representatives 220a to watch the customer's hand movements, see what is behind the customer's back, etc.

As described above, in some embodiments, the transparent panel 210 may include integrated projector components such as liquid crystal projectors, combiners, diffraction gratings, and waveguides to direct images to customer service representatives 220a on the restricted side 200a of the transparent panel 210. In other examples, external projection components 250 may project images that ae reflected off of transparent panel into the field of the vision of a selected customer service representative 220a. In block 804, depending on the particular implementation of the projection components 250 and transparent panel 210, the projection system may be engaged to project the augmented reality elements from or to the appropriate location on the transparent panel 210.

Figure 9:
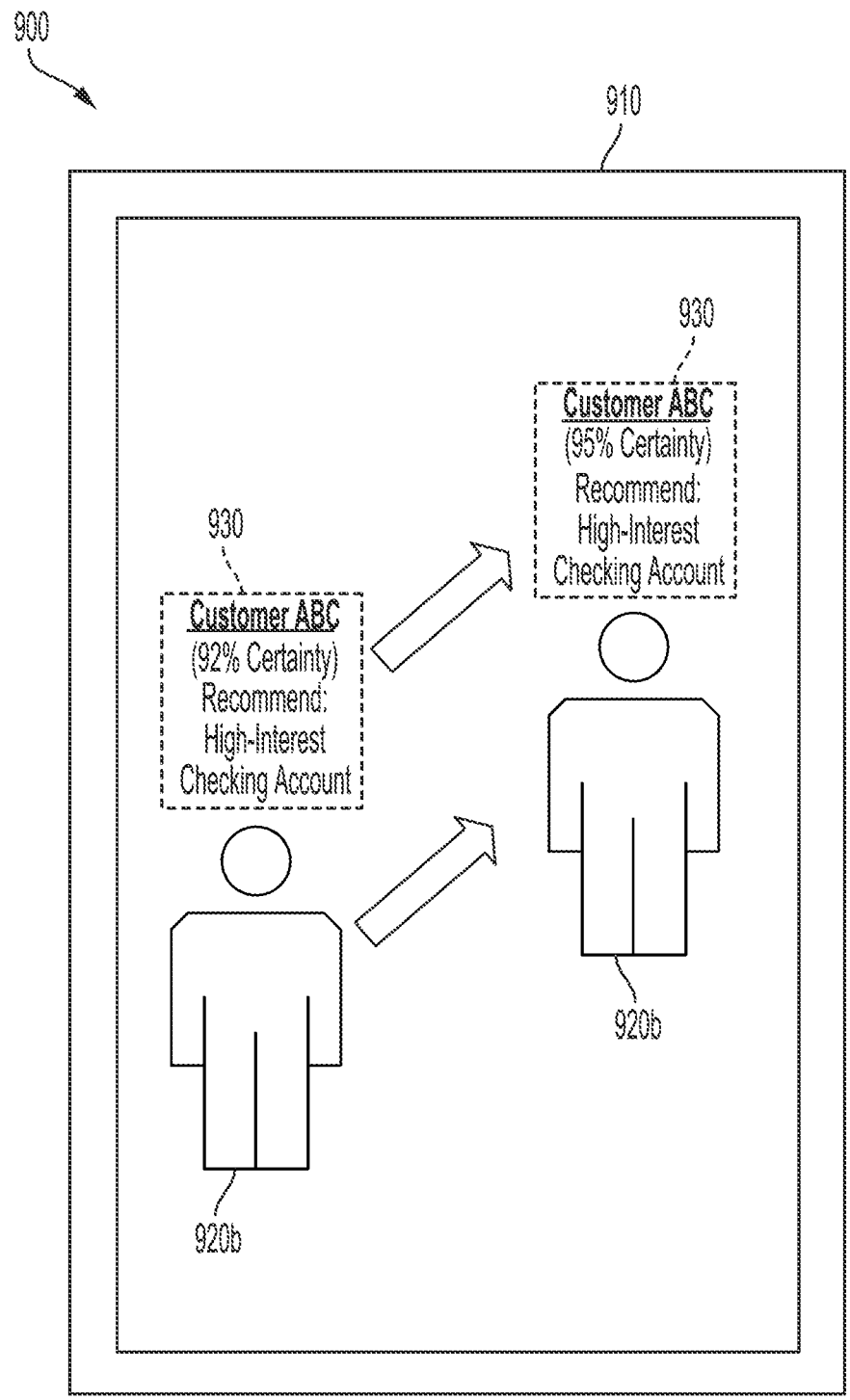
FIG. 9 is a diagram illustrating an example of an augmented reality customer user interface that may be provided to a customer service representative according to some aspects of the present disclosure.

In block 805, after the initial projection of the augmented reality elements containing the customer interaction data, in such a way to be visible to the customer service representative 220a interacting with the customer 220b, the server 302 may continue to track the movement of both the customer 220b and the customer service representative 220a throughout the course of their interaction. User movements may be detected using cameras 306a and other scanning devices 306b at the location 200, including detecting where a customer 220b moves around within the customer side of the location 200, when the customer 220b and/or customer service representative 220a switch customer service windows/locations, when the customer 220b and/or customer service representative 220a sit down, stand up, or shift from left-to-right or right-to left, and so on. In block 806, in response to detected movements by the customer 220b and/or the customer service representative 220a, the server 302 may update the projection of the augmented reality elements. For example, the server 302 may resize and re-position the augmented reality elements 235 so that the augmented reality elements 235 can remain "attached to" the customer 220b from the visual perspective of the customer service representative 220a. Referring briefly to FIG. 9, an example is shown of an augmented reality customer user interface that may be provided to a customer service representative according to some aspects of the present disclosure. In this example, customer service representative is viewing a customer 920b through a transparent panel 910, and the server 302 is projecting an augmented reality element 930 above the customer 920b from the visual perspective of the representative. As shown in this example, as the customer 920b moves around within the customer service location 900, the server 302 updates the size and positioning of the augmented reality element 930 so it remains above the customer 920b from the perspective of the representative. Additionally, as shown in this example, as the customer 920b moves around within the customer service location 900, the server 302 may collect additional data from cameras 306a and scanning devices 306b at the customer service location 900, which may increase the confidence level of the user identification.

In other examples, the server 302 may determine that the interaction between the customer service representative 220a and the customer 220b has ended, and may stop projecting the augmented reality elements 235 associated with that customer 220b. Similarly, the server 302 may determine that the customer service representative 220a has handed off the customer 220b to a different customer service representative 220a and is now interacting with a new customer 220b. In such cases, the server 302 may update the projections of the augmented reality elements so that each customer service representative 220a is able to see the customer interaction data 230 for the customers 220b that the customer service representative 220a is currently interacting with. Additionally, in some embodiments, customer service representatives 220a may update the customer interaction data that is visible via the augmented reality elements 235 during the course of the customer's visit to the location 200. For instance, a representative 220a may update the customer's interaction data 230 based on an initial interaction with the customer 220b to indicate the customer's purpose at the location 200, the customer's current mood, and/or other customer information. Then, when the customer interacts with a second customer service representative 220a, during the same visit to the location 200 (or during a subsequent visit to the same or different locations), then the updated customer interaction data 230 that may be viewed by the second customer service representative may include the updated data added by the first representative regarding the customer's purpose, questions that the customer asked, the customer's mood, or any other customer information that may benefit the second customer service representative 220a in assisting the customer 220b.

The specific operations illustrated in FIG. 8 provide a particular process for generating and providing augmented reality content according to an embodiment. Other sequences of operations may also be performed according to alternative embodiments. For example, alternative embodiments may perform the operations outlined above in a different order. Moreover, the individual operations illustrated in FIG. 8 may include multiple sub-operations that may be performed in various sequences as appropriate to the individual operations. Furthermore, additional operations may be added or removed depending on the particular applications.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. An augmented reality customer interaction system, comprising:
   a transparent panel having a first side and a second side that is opposite to the first side;
   a camera device configured to capture visual data from an area adjacent to the second side of the transparent panel, wherein the visual data includes personally identifying characteristics of a customer located in the area with respect to the second side of the transparent panel; and
   a projection system configured to project information on the first side of the transparent panel, wherein the information comprises customer interaction data retrieved from a data store based on the personally identifying characteristics of the customer, wherein the projection system is configured to project the information only on the first side of the transparent panel such that the information is visible to a first person located in an area adjacent to the first side of the transparent panel, and such that the information is prevented from being viewed by a customer located in the area adjacent to the second side of the transparent panel without obstructing a customer's view through the transparent panel, and wherein the camera device is further configured to track movements of the customer to determine a new location of the customer, and wherein the projection system is configured to:
determine a location on the transparent panel at which the customer interaction data is to be projected based on the new location of customer, and
project the customer interaction data at different locations on the transparent panel based on the movements of the customer such that the customer interaction data follows the movements of the customer and maintains a relationship between a projected location on the transparent panel of the customer interaction data in the new location of the customer, and is visible only to a first person located in an area adjacent to the first side of the transparent panel while the customer is visible to the first person.

2. The augmented reality customer interaction system of claim 1, wherein components of the projection system are integrated into the transparent panel.

3. The augmented reality customer interaction system of claim 1, wherein the camera device is further configured to determine an eye gaze location of a first person on the first side of the transparent panel,
wherein the projection system is configured to project the customer interaction data on the first side of the transparent panel at a location determined by the eye gaze location of the first person.

4. The augmented reality customer interaction system of claim 1, further comprising sensors configured to:
identify a second person in the area adjacent to the first side of the transparent panel; and
determine a second location on the first side of the transparent panel on which the customer interaction data is to be projected, wherein the second location is based on a second location of the customer in the area adjacent to the second side of the transparent surface, and a third location of the second person in the area adjacent to the first side of the transparent surface; and
wherein the projection system is configured to project the customer interaction data at the determined second location on the transparent panel.

5. The augmented reality customer interaction system of claim 1, further comprising sensors configured to:
track movements of a first person in the area adjacent to the first side of the transparent panel and movements of the customer in the area adjacent to the second side of the transparent panel, wherein a location on the first side of the transparent panel on which the customer interaction data is to be projected is determined based on the movements of the customer and the movements of the first person.

6. The augmented reality customer interaction system of claim 1, further comprising:
biometric sensors configured to collect biometric data from the customer;
cameras configured to collect a height measurement of the customer;

cameras configured to collect a gait profile of the customer;
cameras configured to collect ear features of the customer; or
microphones configured to collect a voiceprint of the customer,
wherein a customer profile is determined from customer characteristics stored in a data store based on the biometric data, the height measurement, the gait profile, the ear features, or the voiceprint.

7. The augmented reality customer interaction system of claim 1, wherein the customer interaction data includes strategies for interactions with the customer based on the retrieved data associated with a customer profile, and
wherein the interaction strategies include a product or service offering, or identification of a security risk.

8. A method, comprising:
capturing, with a camera device, visual data from a first area adjacent to a transparent panel, wherein the visual data includes personally identifying characteristics of a customer located in the first area with respect to the transparent panel; and
projecting, with a projection system, information on the transparent panel, wherein the information projected on the transparent panel comprises customer interaction data retrieved from a data store based on the personally identifying characteristics of the customer,
wherein the information is projected on a first side of the transparent panel and the first area in which the customer is located is adjacent to a second side of the transparent panel, and
wherein the information is projected only on the first side of the transparent panel such that the information is visible to a first person located in a second area adjacent to the first side of the transparent panel, and such that the information is prevented from being viewed by a customer located in the first area adjacent to the second side of the transparent panel without obstructing a customer's view through the transparent panel,
wherein the method further comprises:
tracking movements of the customer to determine a new location of the customer;
determining a location on the transparent panel at which the customer interaction data is to be projected based on the new location of customer, and
projecting the customer interaction data on different locations on the transparent panel based on the movements of the customer such that the customer interaction data follows the movements of the customer and maintains a relationship between a projected location on the transparent panel of the customer interaction data in the new location of the customer, and is visible only to a first person located in a second area adjacent to the first side of the transparent panel while the customer is visible to the first person.

9. The method of claim 8, further comprising:
determining an eye gaze location of a first person on the second side of the transparent panel, and
projecting the customer interaction data on the second side of the transparent panel at a location determined by the eye gaze location of the first person.

10. The method of claim 8, further comprising:
identifying a second person in a second area adjacent to the first side of the transparent panel; and
determining a second location on the first side of the transparent panel on which the customer interaction data is to be projected, wherein the second location is based on a second location of the customer in the first area adjacent to the second side of the transparent surface and a third location of the second person in the second area adjacent to the first side of the transparent surface; and projecting the customer interaction data at the determined second location on the first side of the transparent panel.

11. The method of claim 8, further comprising:

tracking movements of a first person in a second area adjacent to the first side of the transparent panel and movements of the customer in the first area adjacent to the second side of the transparent panel; and determining a location on the first side of the transparent panel on which the customer interaction data is to be projected based on the movements of the customer and the movements of the first person.

12. The method of claim 8, further comprising:

collecting biometric data from the customer with biometric sensors;

collecting a height measurement of the customer with one or more cameras;

collecting a gait profile of the customer with the one or more cameras;

collecting ear features of the customer cameras with the one or more cameras; or collecting a voiceprint of the customer with one or more microphones; and determining a customer profile from customer characteristics stored in a data store based on the biometric data, the height measurement, the gait profile, the ear features, or the voiceprint.

13. The method of claim 8, wherein the customer interaction data includes strategies for interactions with the customer based on the retrieved data associated with a customer profile, and wherein the interaction strategies include a product or service offering, or identification of a security risk.

* * * * *